(12) United States Patent
Guala

(10) Patent No.: US 7,784,766 B2
(45) Date of Patent: Aug. 31, 2010

(54) VALVE CONNECTOR FOR MEDICAL INFUSION LINES

(75) Inventor: Gianni Guala, Turin (IT)

(73) Assignee: Industrie Borla S.p.A., Moncalieri (Turin) (IT)

( * ) Notice: Subject to any disclaimer, the term of this patent is extended or adjusted under 35 U.S.C. 154(b) by 270 days.

(21) Appl. No.: 11/572,747

(22) PCT Filed: Jul. 13, 2005

(86) PCT No.: PCT/IB2005/002206

§ 371 (c)(1),
(2), (4) Date: Jan. 18, 2008

(87) PCT Pub. No.: WO2006/013433

PCT Pub. Date: Feb. 9, 2006

(65) Prior Publication Data

US 2008/0190485 A1     Aug. 14, 2008

(30) Foreign Application Priority Data

Jul. 27, 2004   (IT) ........................ TO2004A0524

(51) Int. Cl.
*F16K 51/00* (2006.01)
(52) U.S. Cl. .................................. 251/149.6; 604/249
(58) Field of Classification Search .............. 251/149.3, 251/149.7, 149.6; 604/249, 533
See application file for complete search history.

(56) References Cited

U.S. PATENT DOCUMENTS

| | | | | | |
|---|---|---|---|---|---|
| 5,242,393 | A | * | 9/1993 | Brimhall et al. | ................ 604/86 |
| 5,807,348 | A | * | 9/1998 | Zinger et al. | ................ 604/246 |
| 6,019,748 | A | * | 2/2000 | Lopez | ......................... 604/249 |
| 6,079,432 | A | | 6/2000 | Paradis | ........................... 137/1 |
| 6,206,861 | B1 | | 3/2001 | Mayer | ........................ 604/246 |
| 6,682,509 | B2 | | 1/2004 | Lopez | ......................... 604/249 |
| 6,964,406 | B2 | * | 11/2005 | Doyle | ...................... 251/149.6 |
| 2002/0153503 | A1 | * | 10/2002 | Newton et al. | ........... 251/149.1 |
| 2003/0098430 | A1 | | 5/2003 | Leinsing et al. | ......... 251/149.6 |
| 2005/0038397 | A1 | * | 2/2005 | Newton et al. | .............. 604/249 |

FOREIGN PATENT DOCUMENTS

WO    WO 2005/011779    2/2005

* cited by examiner

*Primary Examiner*—John K Fristoe, Jr.
*Assistant Examiner*—Marina Tietjen
(74) *Attorney, Agent, or Firm*—Heslin Rothenberg Farley & Mesiti P.C.; Victor A. Cardona, Esq.

(57) ABSTRACT

A valve connector for medical infusion lines includes an external tubular body with an inlet end and an outlet end, a hollow internal pin and an intermediate elastic sealing member 3 having a head with pre-slotting and an elastic hollow element abutted radially against the hollow pin. The hollow pin has a closed terminal shaped, as a result of the insertion of a fluid introducer into the inlet end, in such a way as to make the elastic head assume an elastically deformed configuration without crossing the pre-slotting, which is opened to place in communication the inlet end with the outlet end through lateral holes of the hollow pin.

22 Claims, 15 Drawing Sheets

VALVE CONNECTOR FOR MEDICAL INFUSION LINES

CROSS REFERENCE TO RELATED APPLICATION

This application is a 371 national stage filing of PCT International Application No. PCT/IB2005/002206, filed on 13 Jul. 2005, and published in England on 9 Feb. 2006, as WO 2006/013433 which claims priority to TO2004A000524 filed on 27 Jul. 2004, the entire disclosures of which are incorporated herein by reference.

FIELD OF THE INVENTION

The present invention relates to valve connectors for medical infusion lines by means of an introducer of a fluid infusion, typically a Luer or Luer-Lock union fitting for example of a syringe of the needle-less type.

BACKGROUND ART

Valve connectors of this type are known, e.g. from the documents U.S. Pat. Nos. 5,242,342, 5,676,346, 6,706,022, 5,700,248 and 6,682,509.

More in particular, the documents U.S. Pat. Nos. 5,700,248 and 6,682,509 describe a valve connector according to the preamble to claim 1, which provides a tubular body having a cavity, an inlet end adapted for the engagement of an introducer of liquid, and an outlet end. A hollow pin is arranged axially within the cavity of the tubular body and has a closed terminal oriented towards the inlet end of the tubular body and axially distanced therefrom. The hollow pin is in communication with the outlet end of the tubular body and has at least a lateral hole distanced from its terminal for communication with the cavity of the tubular body. The connector further includes an elastic sealing member which comprises an elastic head having a pre-slotting and normally arranged in a closed condition (or inactive condition) within the inlet end of the tubular body in which the pre-slotting is closed, and axially movable against the terminal of the hollow pin by effect of the insertion of said introducer into the inlet end, to interact with said terminal assuming an elastically deformed open configuration (or active condition) in which the pre-slotting is opened. The elastic sealing member of the valve connector further comprises an elastic hollow element joined to the head and interposed between the tubular body and the hollow pin to isolate the cavity of the tubular body relative to its outlet end. Said elastic hollow element defines an elastic thrust means which tends to maintain the head in its closed condition, and has an internal contact surface with the hollow pin to isolate the aforesaid at least one lateral hole relative to the cavity of the tubular body when the head is in the closed condition.

Valve connectors of this type must meet a series of fundamental requirements, since their use is often critical for the survival of the patients who utilize them.

In the first place, the closure of the inlet end of the tubular body operated by the head of the elastic member must be substantially tight, thereby assuring a total anti-bacterial barrier, even after repeated opening and re-closings of the valve connector.

Secondly, the opening and re-closing operation of the communication between the inlet end and the outlet end of the connector upon the insertion and respectively of the extraction of the introducer must be wholly reliable and repeatable without even minimal risk of malfunctions which could entail severe risks for the patient connected to the valve connector. For this reason, the number of moving mechanical member of the valve connector must be as small as possible.

Thirdly, these connectors must be able effectively to support any over-pressures which may be generated within them in sue and in the closed or inactive condition, and assure an effective seal against positive and negative.

Lastly, these valve connectors must be easily cleaned and disinfected from the side of the inlet end, typically with a wad imbued with disinfectant.

In the case of the valve connectors known from the aforementioned documents U.S. Pat. Nos. 5,700,248 and 6,682,509, the opening of the communication between the inlet end of the tubular body and the outlet end, through the lateral hole or holes of the hollow pin upon the engagement of the introducer, is achieved as a result of the crossing of the pre-slotting of the elastic head by the terminal of the hollow pin. The hollow element of the elastic member has a corrugated or bellow-shaped wall, so that its axial compression produces a collapse thereof in the manner of an accordion. The axial compression of the hollow element is such that the elastic head flows along the hollow pin until it is positioned below the lateral hole or holes thereof, thereby directly exposing these lateral holes to the flow coming from the introducer.

This arrangement essentially has the drawback that the sealing of the lateral hole or holes of the hollow pin, in the condition of closure of the valve connector, is entrusted solely to the radial elasticity of the hollow element of the elastic member. Moreover, the crossing of the pre-slotting of the elastic head by the terminal of the hollow pin upon opening the valve connector, together with the engagement of the related closed terminal into the introducer, may entail risks of malfunctions in addition to limitations in relation to the minimum diameter of the introducers which can be used with said known valve connectors.

DISCLOSURE OF THE INVENTION

The object of the present invention is to overcome the aforesaid drawback, and said object is essentially achieved thanks to the following combination of characteristics:
- the terminal of the hollow pin is so shaped as to cause the head of the elastic sealing member assume the aforesaid open configuration without crossing the pre-slotting,
- the tubular body positively presses the inner contact surface of the hollow element of the elastic sealing member against the hollow pin when the aforesaid elastic head is in the closed position,
- when said elastic head moves from the closed condition to the open configuration, the inner contact surface of the hollow element of the elastic sealing member opens communication between the aforesaid at least one lateral hole of the hollow pin and the inlet end of the tubular body through said pre-slotting.

Thanks to this solution idea, the aforementioned drawbacks of known valve connectors are effectively overcome, with appreciable advantages in terms of greater safety, functionality and versatility of use.

Preferably, the tubular body of the connector has a portion of inner wall with conical surface against which, in the non deformed condition of seal of the elastic head, contrasts a portion with conical surface complementary to the outer surface of the hollow element of the elastic sealing member. A radial thrust component is thereby achieved of the inner surface of the hollow element of the elastic sealing member against the outer surface of the hollow pin, thereby assuring an effective and secure isolation of the aforesaid at least one lateral hole of the hollow pin. This effect can be further improved thanks to the fact that the hollow element of the elastic sealing member tends to press the elastic head in the aforesaid non deformed sealing condition against the action of an axial pre-load.

According to an additional advantageous characteristic of the invention, the hollow element of the elastic sealing element consists of a generally cylindrical, non corrugated body.

In a first embodiment of the invention, the inner contact surface of the hollow element of the sealing elastic element is shaped in such a way as to be applied against the aforesaid at least one lateral hole of the hollow pin in the aforesaid non deformed sealing condition. In this case, the hollow pin can be formed, at said at least one lateral hole, with an external annular throat.

In a variant, currently considered the preferred embodiment, the inner contact surface of the hollow element of the elastic sealing member is shaped in such a way as to be applied, in the aforesaid non deformed sealing condition, at a region of the hollow pin that is situated between said at least one lateral hole and said terminal.

BRIEF DESCRIPTION OF THE DRAWINGS

The invention shall now be described in detail with reference to the accompanying drawings, provided purely by way of non limiting example, in which.

DETAILED DESCRIPTION OF THE INVENTION

Figure 1:
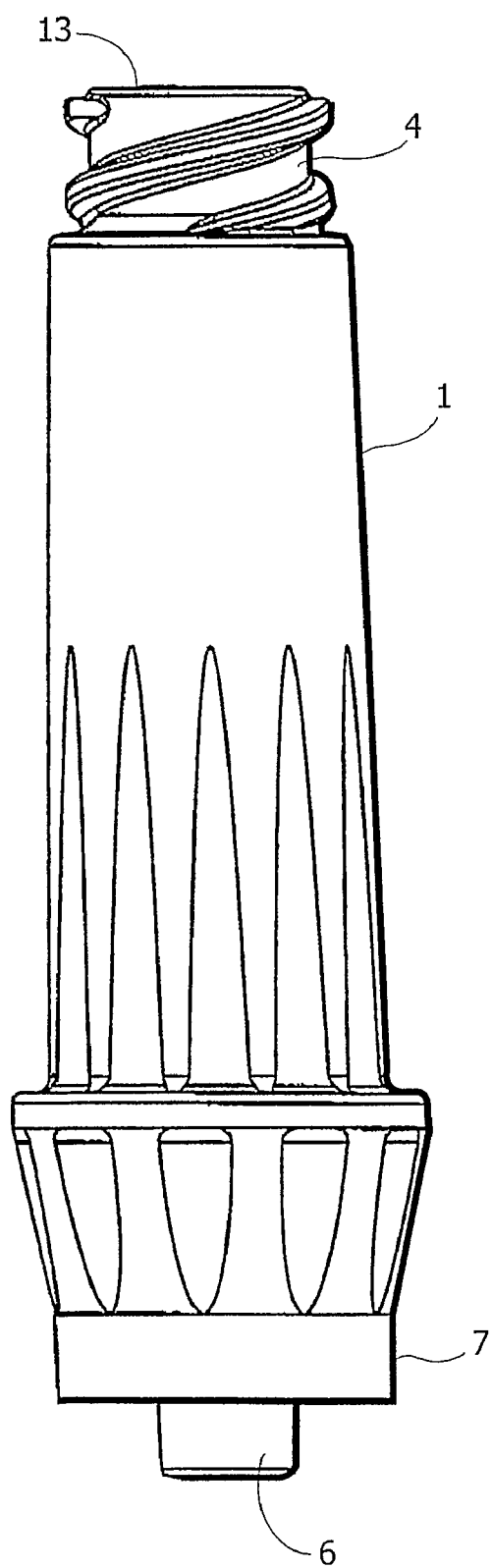
FIG. 1 is a schematic side elevation view of a valve connector for medical lines according to the invention.
Figure 2:
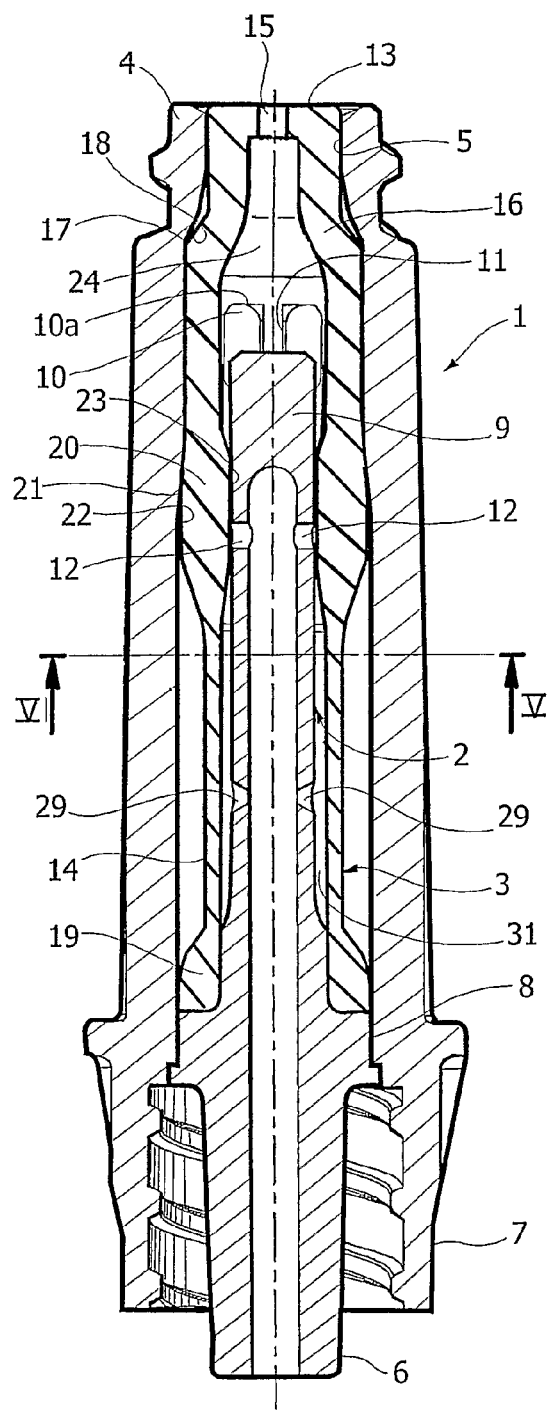
FIG. 2 is a schematic axial section view of the valve condition in a first embodiment of the invention, shown in a first condition.

Referring initially to FIGS. 1 and 2, a first embodiment of the valve connector for medical infusion lines according to the invention essentially comprises an external tubular body 1, a hollow internal pin 2 positioned axially within the cavity of the tubular body 1, and an intermediate elastic sealing member 3. Typically, the tubular body 1 and the hollow pin 2 are made of molded plastic material, whilst the elastic sealing element is made of an elastic material, e.g. silicone rubber.

Figure 3:
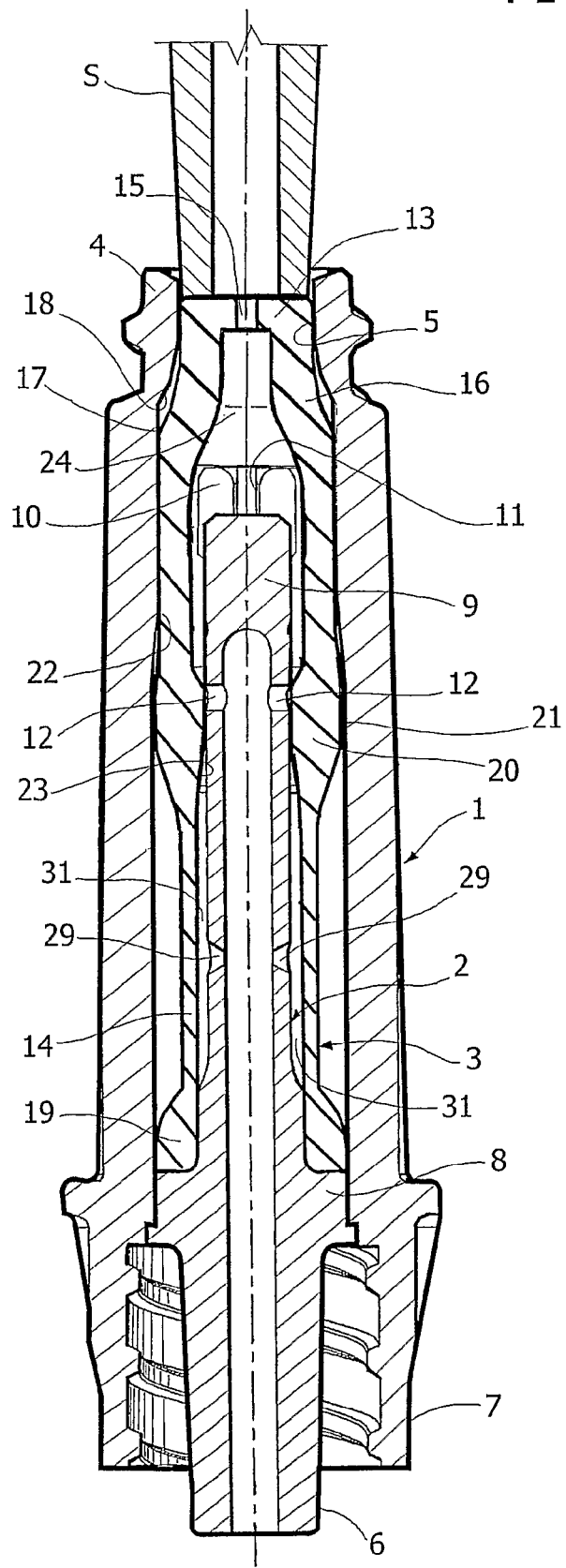
FIGS. 3 and 4 are two similar views to FIG. 2, showing two different operative conditions of the valve connector.
Figure 4:
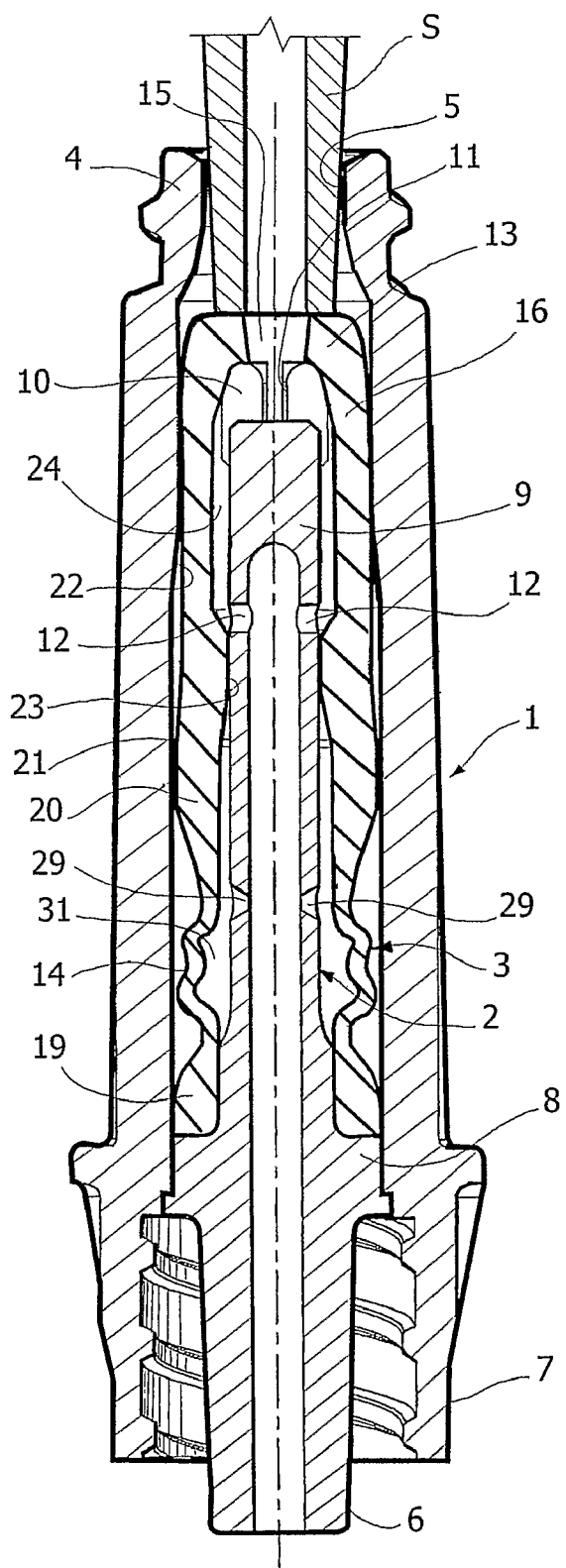

The external tubular body 1 has an inlet end 4 formed in the manner of a female Luer-Lock connecting member for the engagement, in generally conventional fashion, with a male Luer or Luer-Lock connecting member of a fluid introducer, constituted for example by a needle-less syringe, a part whereof is schematically designated by the reference S in FIGS. 3 and 4. The inner annular surface of the inlet end 4, designated by the reference 5, can be only slightly conical or also, more conveniently, cylindrical.

Figure 8:
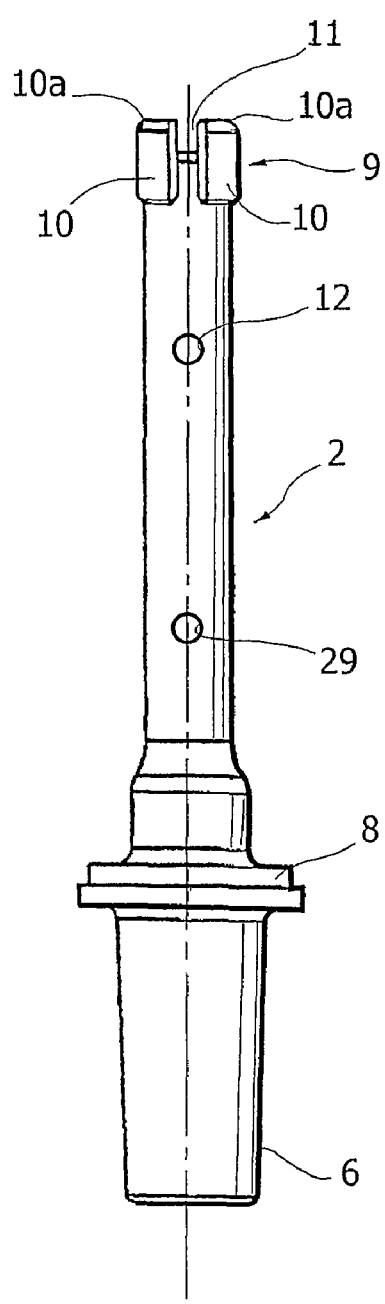
FIG. 8 is an elevation view of a component of the valve connector according to a first embodiment.
Figure 9:
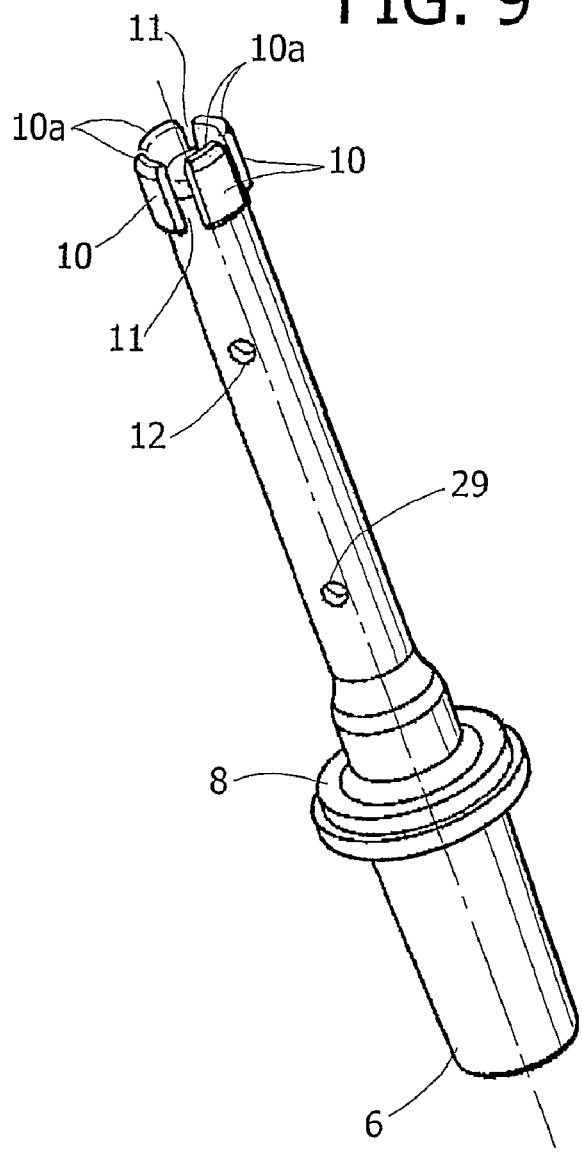
FIG. 9 is a perspective view of FIG. 8.
Figure 10:
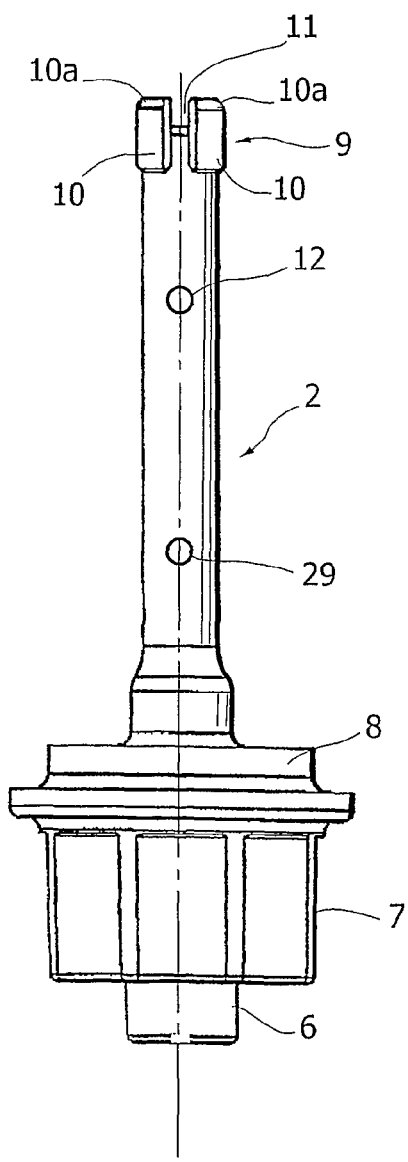
FIG. 10 is a similar view to FIG. 8, showing a second embodiment of the same component.
Figure 11:
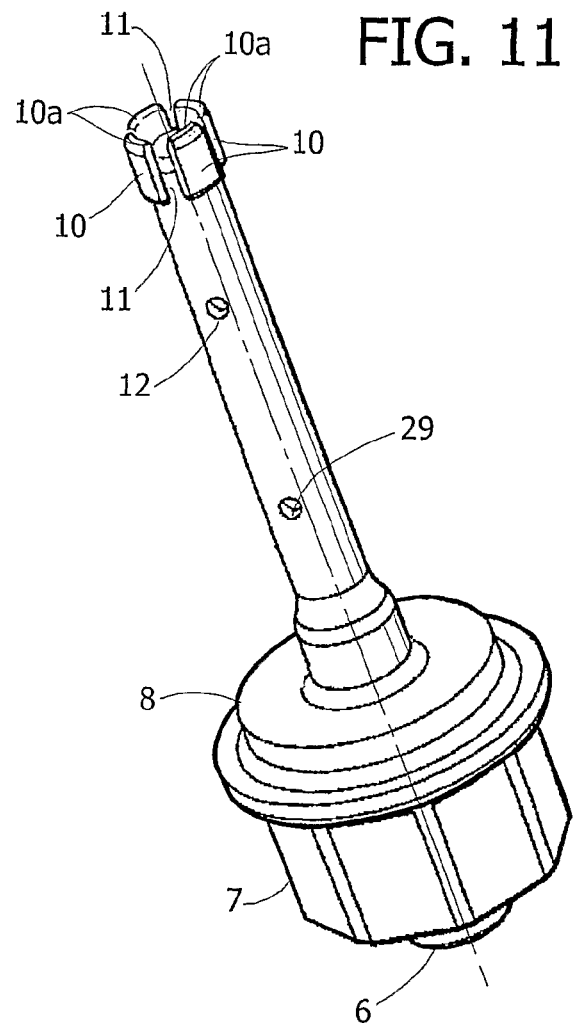
FIG. 11 is a perspective view of FIG. 10.

The other end of the tubular body 1, or the outlet end, is shaped in the manner of a male Luer-Lock connecting organ with a central tubular spigot 6 with slightly conical outer surface 7 and an internally threaded outer cladding 7. In the embodiment of FIG. 2, the outer cladding 7 is obtained integrally with the tubular body 1, whilst the inner spigot 6 is formed integrally with the hollow pin 2, as shown in FIGS. 8 and 9. In the junction region between the hollow pin 2 and the spigot 6 is provided an annular flange 8 which is coupled in sealed fashion within the tubular body 1 in the immediate vicinity of the threaded cladding 7. In a variant, shown in FIGS. 10 and 11, both the central spigot 6 and the threaded cladding 7 are obtained integrally with the hollow pin 2, which in this case as well is formed with the annular flange 8 for coupling within the tubular body 1.

Figure 7:
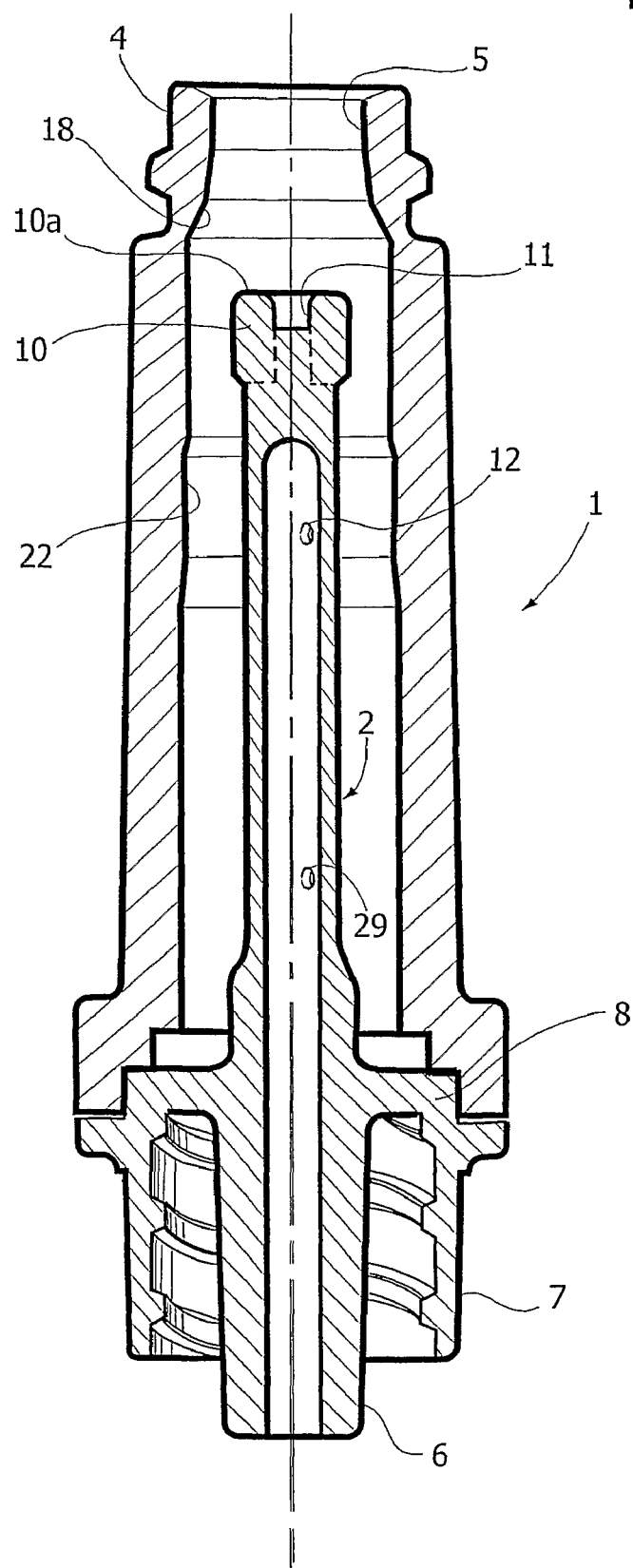
FIG. 7 is a similar view to FIG. 2, but rotated by about 30°, in which a component of the connector is omitted.

The hollow pin 2 has, at the side opposite the outlet end 6, 7 of the connector, a closed terminal 9 oriented towards the inlet end 4 and situated at a short axial distance therefrom. Differently from some known valve connectors in which the free end of the hollow pin has a perforating tip, the terminal 9 is formed with a crown of axial-radial projections 10, angularly distanced in such a way as to define between them external axial-radial flow channels 11. Said flow channels 11 are more clearly visible in FIGS. 8, 9 and 10, 11, and also in FIG. 7, which corresponds to FIG. 2 with the exception that the conformation of the outlet end 6, 7 is that of FIGS. 10 and 11 instead of that of FIGS. 8 and 9, and in which the elastic sealing member 3 was omitted for the sake of simplicity of illustration.

The end surfaces 10a of the projections 10 oriented towards the inlet end 4 are preferably planar or slightly rounded.

At a short distance from the terminal 9, the hollow pin 2 is formed with one or more radial lateral holes 12 through which the cavity of the pin 2, and hence the outlet end 6, 7 of the valve connector, can be placed in communication, in the manners clarified below, with the inlet end 4.

Figure 12:
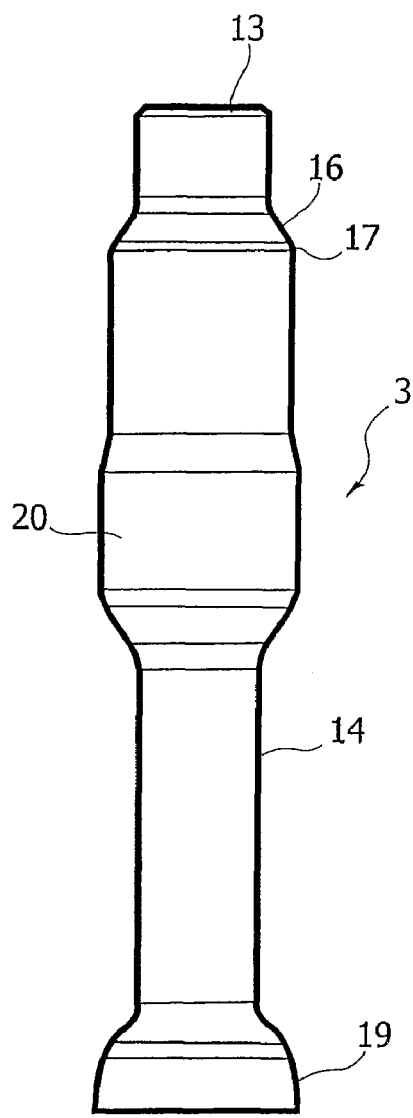
FIG. 12 is an elevation view of another component of the valve connector, and in particular of the one omitted in FIG. 7.
Figure 13:
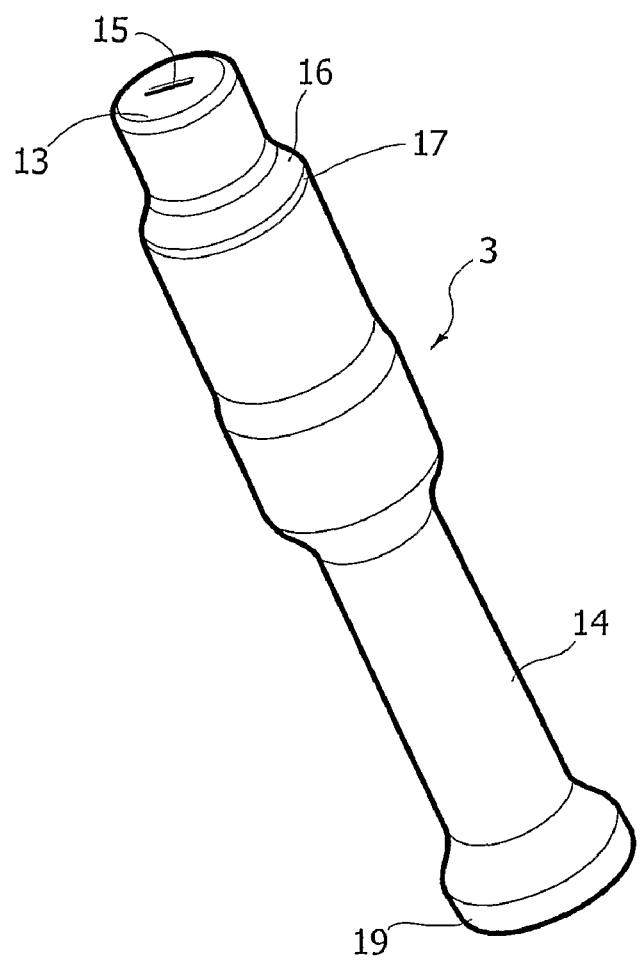
FIG. 13 is a perspective view of FIG. 12.

As FIGS. 12 and 13 more clearly show, the sealing elastic member 3 comprises, conveniently in a single piece, an elastic head 13 and an elastic hollow element 14.

The elastic head 13 has a complementary shape to that of the inner wall 5 of the inlet fitting 4 in such a way as to be able to be housed therein, in the manner shown in FIG. 2, in contact without substantial interference in a closed condition in which said head 13 is substantially undeformed. Or, when the elastic head 13 closes the inlet end 4, it is substantially not compressed within the inner surface 5 thereof.

Through the head 13 is formed a pre-slotting or axial notch 15 which, in the non deformed closed condition of the elastic head 13 within the inlet end 4, is shut by effect of the elasticity of the head 13. In this condition, an anti-bacterial protection barrier is achieved between the interior of the valve connector and the exterior, whilst assuring the possibility of an effective cleaning operation, conventionally conducted by means of a wad imbued with a disinfectant.

The head 13 joins the elastic hollow element 14 through a cone frustum portion 16 whose greater base defines an annular arresting shoulder 17 which, in the non-deformed condition of sealing of FIG. 2, faces an inner annular shoulder 18 with conical surface, complementary to the tubular body 1.

Figure 5:
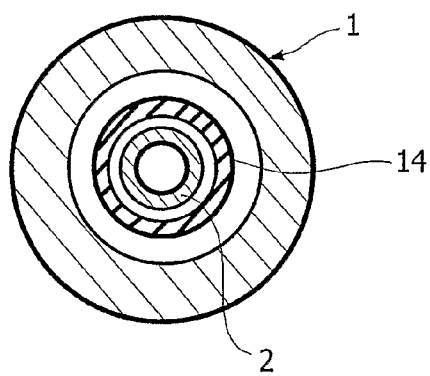
FIG. 5 is a cross section view according to the line V-V of FIG. 2.
Figure 6:
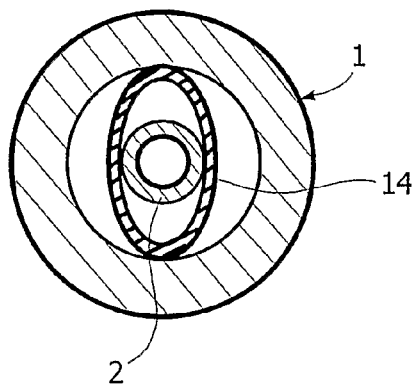
FIG. 6 is a variant of FIG. 5.

Said hollow elastic element 14 has, at the opposite side from the elastic head 13, an end lip 19 which is closed in sealed fashion against the outer wall of the hollow pin 2 at the annular flange 8 thereof. The general configuration of the elastic hollow element 14 can be corrugated or bellows shaped (as in the case of the aforementioned documents U.S. Pat. Nos. 5,700,248 and 6,682,509) or, much more conveniently and simply, with simply cylindrical shape, with circular section (as shown in detail in FIG. 5), elliptical (as shown in detail in FIG. 6), or even polygonal. In any case the elastic hollow element 14 has a thickened portion 20 with slightly conical outer surface 21 co-operating, in the manners clarified below, with a complementary conical surface portion 22 of the inner wall of the tubular body 1. The inner wall of the portion 20 of the elastic hollow element 14, designated by the reference 23, is arranged in contact with the hollow pin 2 and, in the undeformed closed condition of the head 13 within the inlet fitting 4, it closes in sealed fashion the lateral holes 12 in such a way as to isolate the outlet fitting 6, 7 of the chamber 24 between the elastic head 13, the closed terminal 9 and the region of the inner wall of the elastic member 3 that surrounds the terminal 9. The sealed closing of the lateral holes 12 by the inner wall 23 is assured, according to a peculiar aspect of the invention, by the circumferential radial abutting thereof against the hollow pin 2, operated by effect of the interaction between the conical surfaces 21 and 22 and under the action of an axial elastic pre-loading of the elastic hollow element 14.

The operation of the valve connector thus described is as follows.

In the closed condition shown in FIG. 2, the elastic head 13 is, as stated, in non deformed closing configuration within the inlet end 4, with the pre-slotting 15 maintained hermetically closed. The axial pre-load of the elastic hollow element 14, in co-operation with the radial thrust component applied positively by the inner section with conical surface 22 of the tubular body 1 against the conical outer surface section 21 of the elastic hollow element 14, maintains as stated the portion 20 of said hollow element 14 in contact with hermetic closure of the lateral holes 12 of the hollow pin 2. In this way, the communication between the inlet end 4 and the outlet end 6, 7 of the valve connector is doubly shut at one side by effect of the closure of the inlet fitting 4 by the elastic head 13 in the non deformed condition, and at the other side by the occlusion of the holes 12 by the portion 20 of the elastic hollow element 14.

When the end of the needle-less syringe S is frontally coupled in sealed fashion against the elastic head 13 and then inserted into the inlet fitting 4, in the manner shown in FIG. 3, the elastic head 13 is thrust axially towards the interior of the connector, by effect of the compression or axial collapse of the elastic hollow element 14. Simultaneously, the section 20 of the hollow elastic element 14 slides along the hollow pin 3 in the direction of the outlet fitting 6, 7, freeing the lateral holes 12 which are thereby placed in communication with the chamber 24.

The surface 5 is designed specifically to be deformed and house in sealed fashion the conical surface of the syringe S, being cylindrical or with reduced conicity.

Continuing the introduction of the needle-less syringe S, until its complete locking to the Luer-Lock connection on the inlet fitting 4, the valve connector assumes the configuration shown in FIG. 4: the additional axial compression of the elastic hollow element 14 allows the head 13 to translate forward towards the interior of the hollow body 1 until it contrasts frontally against the terminal 9, thereby interacting with the projections 10 thereof. By effect of said interaction, the head 13 assumes an elastically deformed, i.e. radially dilated outwards, configuration, in such a way as to open the pre-slotting 15. In this way, the inlet fitting 4, or the needle-less syringe S, are placed in communication with the outlet fitting 6, 7 through the chamber 24, the channels 11 of the terminal 9, the lateral holes 12 and the cavity of the hollow pin 2.

When the needle-less syringe S is extracted from the input fitting 4, the elastic return of the hollow element 14 of the elastic sealing 3 promptly restores the sealed configuration of FIG. 2, in which the elastic head 13 returns to the undeformed condition within the inlet fitting 4, which in turn elastically returns to the undeformed condition, and the lateral holes 12 are re-closed by the section 20 of the elastic hollow element 14.

Figure 14:
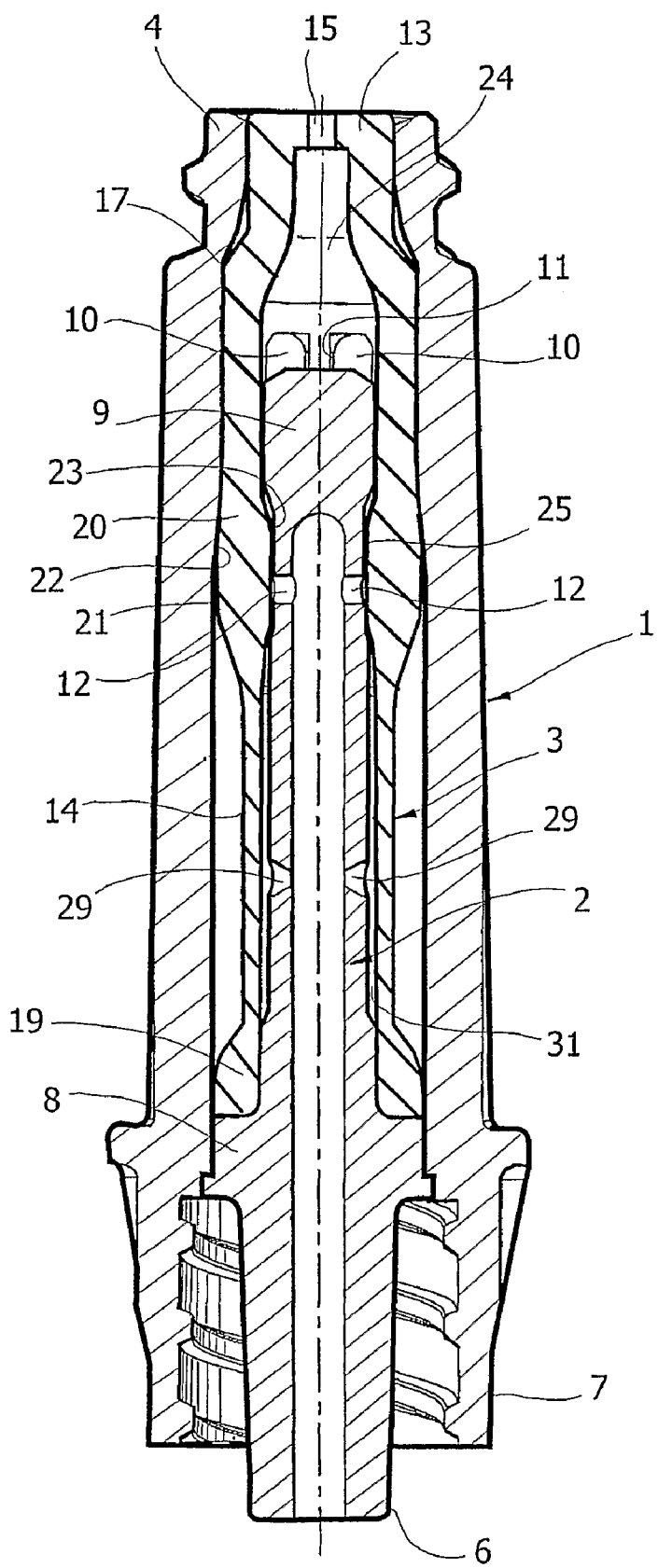
FIG. 14 is a similar view to FIG. 2, showing a first variant of the valve connector in a first operative condition.
Figure 15:
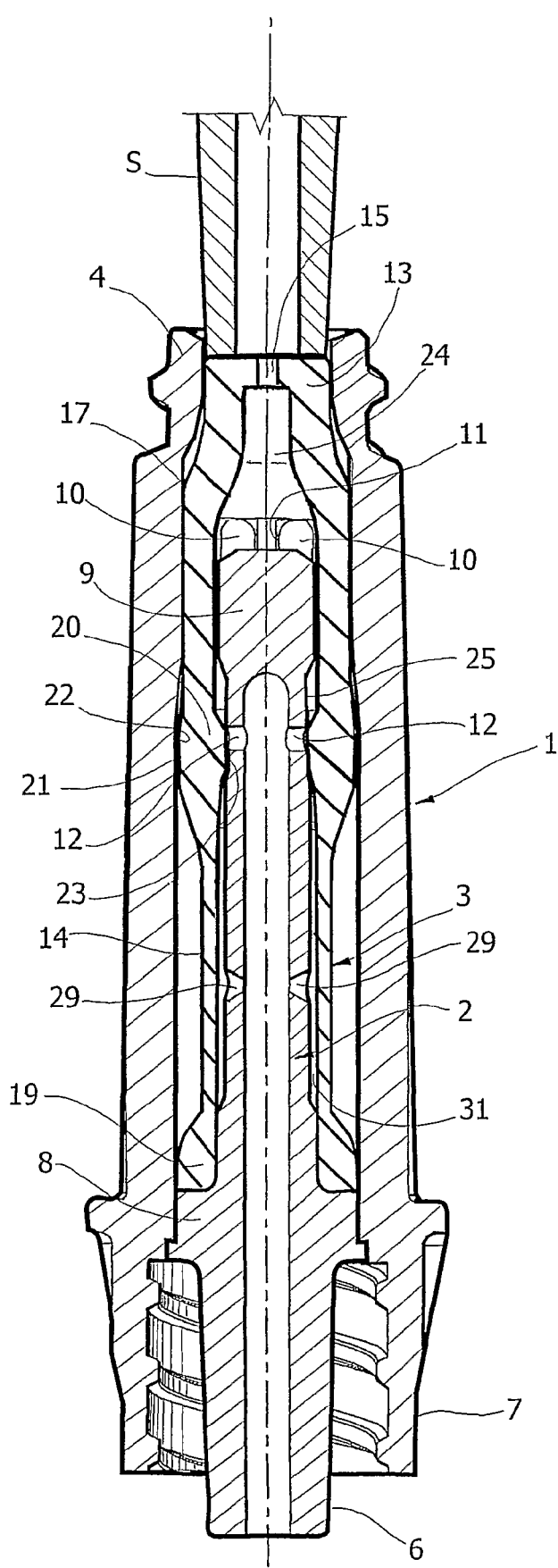
FIGS. 15 and 16 are two similar views to FIG. 14, showing two different operative conditions of the valve connector.
Figure 16:
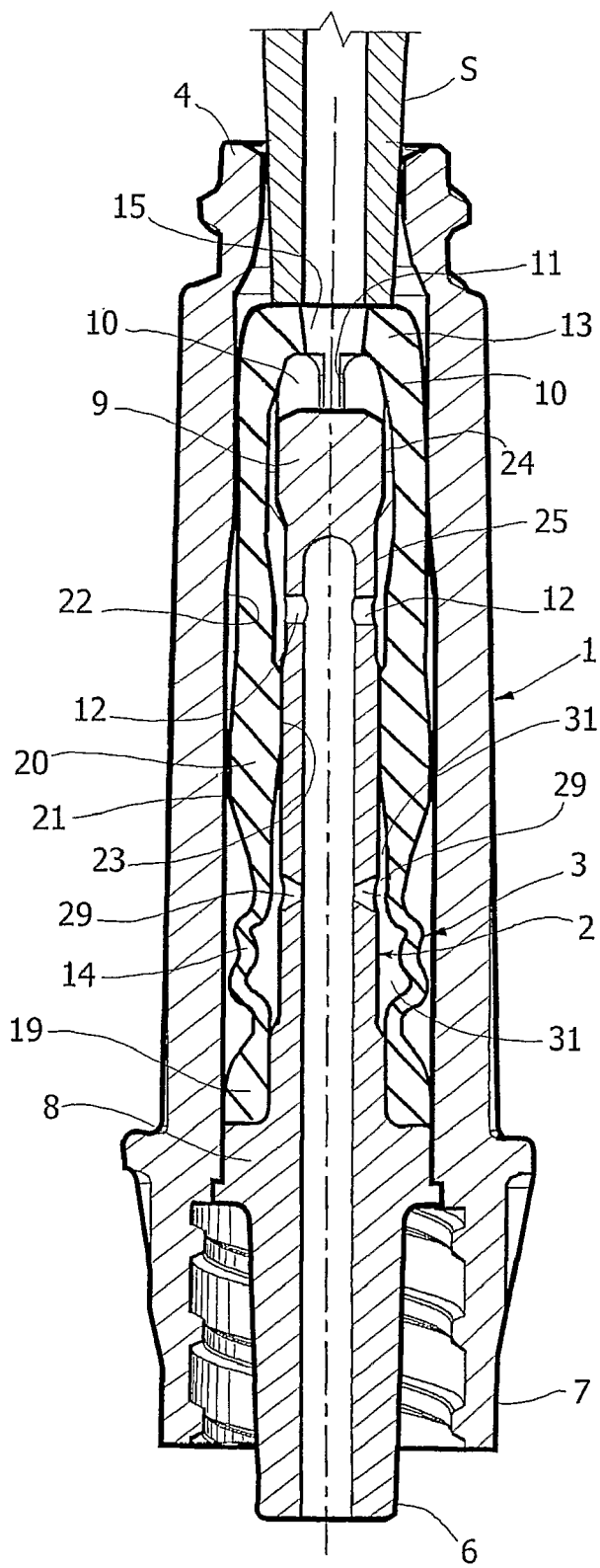

FIGS. 14 through 16 show a variant of the valve connector according to the invention in the same three operative conditions described previously with reference to FIGS. 2 through 4. In this variant, parts that are identical or similar to those already described above are designated by the same numerical references.

In fact, the variant consists solely of the fact that the hollow pin 2 is formed, at the lateral holes 12, with an annular depression or throat 25, of more or less extended axial length, into which is engaged, in the undeformed condition of sealing of the elastic head 13 in the input fitting 4, the thickened section 20 of the elastic hollow element 14 of the elastic sealing member 3. In this variant as well, as a result of the introduction of the needle-less syringe S into the inlet fitting 4 and of the consequent axial compression of the elastic hollow element 14, the section 20 progressively translates towards the outlet fitting 6, 7 sliding along the hollow pin 2, thereby freeing the lateral holes 12. By effect of the elastic deformation of the head 13 due to the interaction with the projections 10 of the terminal 9, the flow communication between the inlet fitting 4 and the outlet fitting 6, 7 then opens through the open pre-slotting 15, the chamber 24, the flow channels 11, the holes 12 and the cavity of the hollow pin 2, as shown in FIG. 16.

Figure 17:
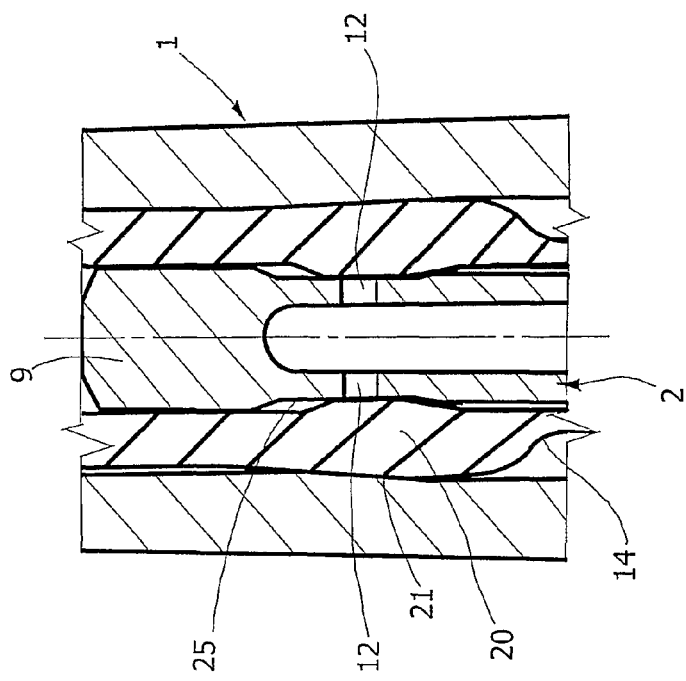
FIG. 17 shows a detail of FIG. 14 in enlarged scale.

FIG. 17 shows the detail of the hermetic closure of the holes 12 by the section 20 of the elastic hollow element 14 in the sealed condition of FIG. 14.

Figure 18:
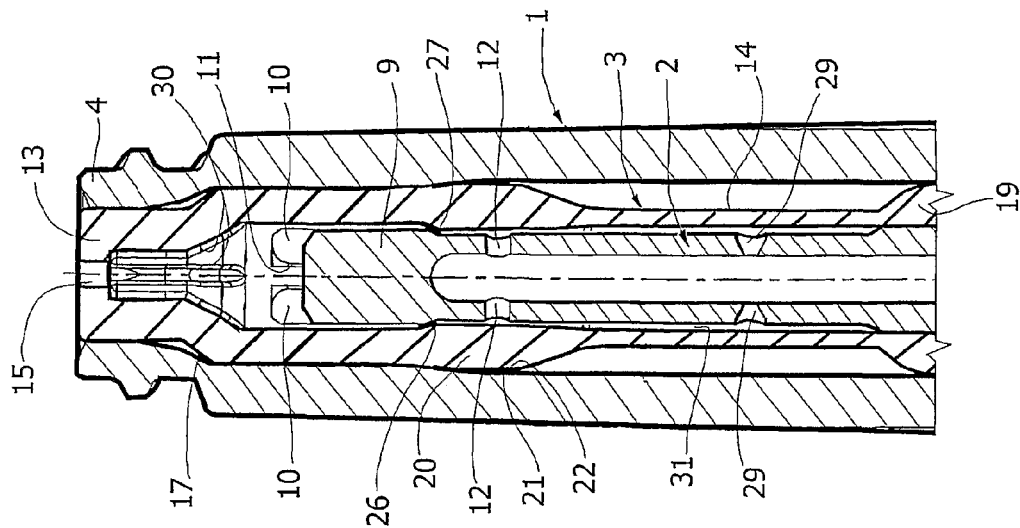
FIG. 18 is a view, similar to FIGS. 2 and 14 and partial, showing a second variant of the valve connector according to the invention.
Figure 19:
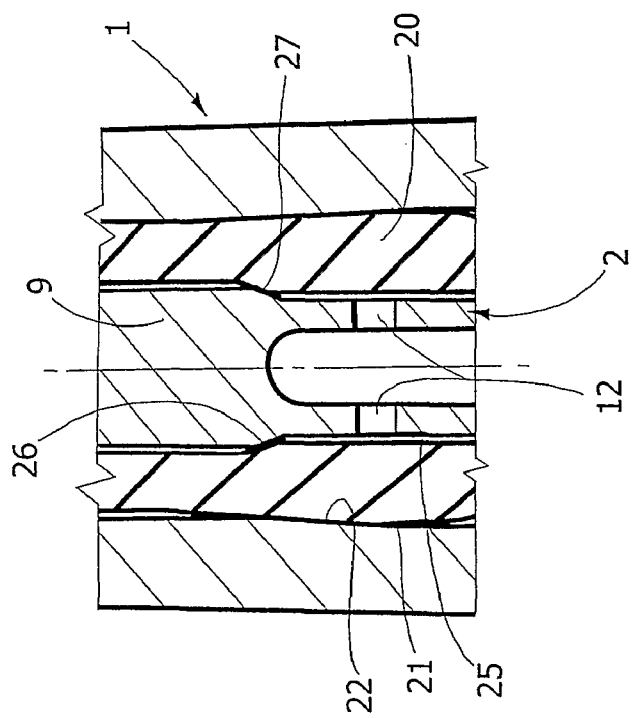
FIG. 19 shows an enlargement of FIG. 18.
Figure 21:
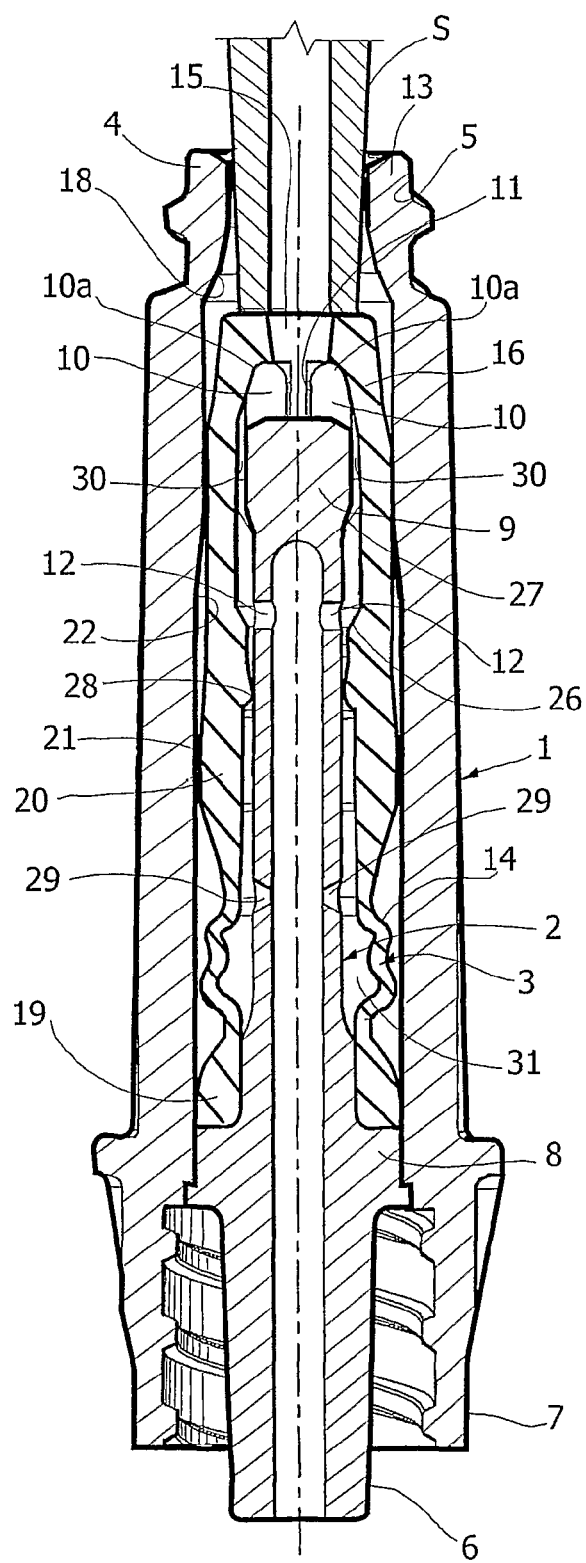
FIG. 21 is similar view to FIG. 20, with the valve connector in open condition.

An additional variant of the valve connector according to the invention is shown in FIGS. 18 and 19. In this variant, in which parts that are identical or similar to those already described previously are designated by the same numeric references, the section 20 of the hollow elastic element 14 of the elastic sealing member 3 achieves the hermetic closure of the lateral holes 12 of the hollow pin 2 in indirect rather than direct fashion. I.e., instead of closing against the surface of the annular throat 25, the section 20 has a portion with conical surface 26 which, in the sealing condition, is pressed in sealing contact against a complementary external conical surface 27 serving as a junction with the annular depression 25. Said sealing contact in this case is assured both by the axial pre-load of the elastic hollow element 14, and by the axial and radial components of the thrust applied positively by the inner conical surface 22 of the tubular body 1 against the external conical surface 21 of the elastic hollow element 14. In this variant, as in the one that will be described below, the inner surface of the elastic head 13 is formed with a crown of channels 30 which, in the open condition of the head 13, define axial flow passages for conveying the fluid coming from the syringe S from the radial passages 11, defined between the projects 10 of the terminal 9 of the hollow pin 2, to the lateral holes 12 (see for example also FIG. 21).

Figure 22:
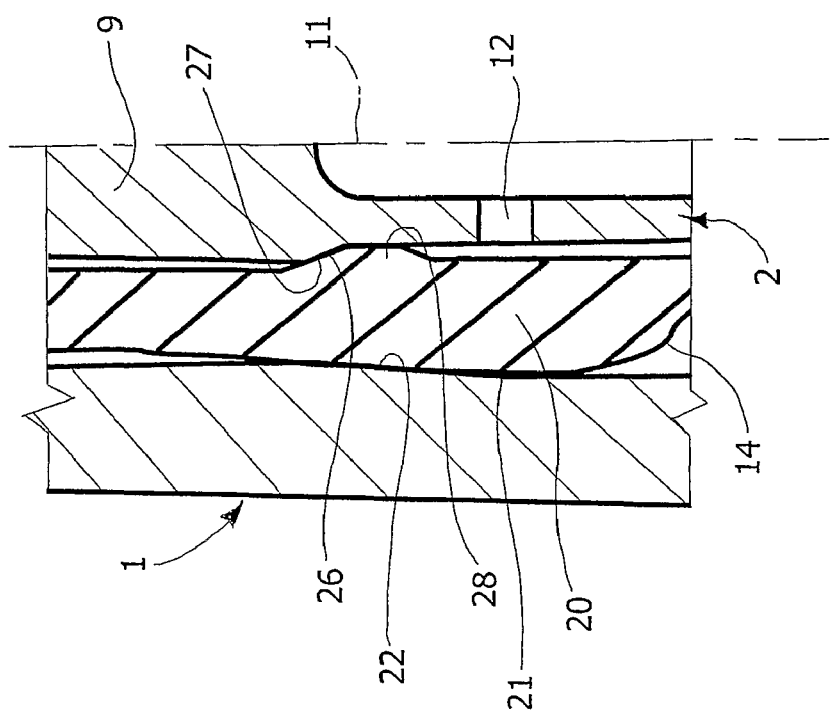
FIG. 22 shows a detail of FIG. 20 in enlarged scale.
Figure 20:
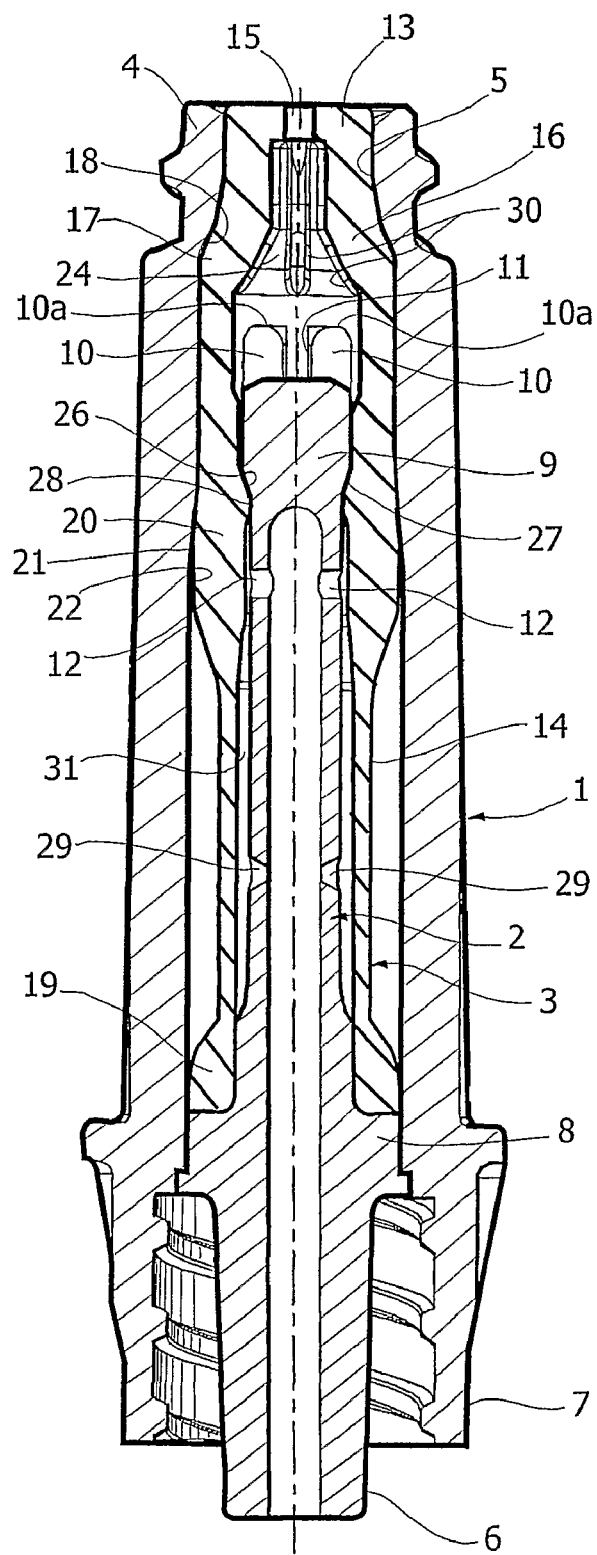
FIG. 20 is a similar view to FIGS. 2 and 14, showing a third variant of the valve connector according to the invention, represented in the closed condition.

In the additional variant shown in FIGS. 20 and 22, currently considered the preferred embodiment and in which parts that are identical or similar to those already described previously are designated by the same numeric references, the inner conical surface 26 of the hollow elastic element 14 co-operating with the outer conical surface 27 of the hollow pin 2 is formed by an inner annular projection 28 of said elastic hollow element 14.

This variant is, as stated, currently considered preferred essentially because the abutment of the inner annular projection 28 against the conical outer surface 27 of the hollow pin 2, in the condition of closure of the valve connector, is still more secure even if, in use, a vacuum or an overpressure is generated within the connector.

In all the embodiments of the valve connector described above, the hollow pin 2 can be provided with additional lateral holes 29, axially distanced from the lateral holes 12 and having the function of placing in communication the outlet fitting 6, 7 with the inner chamber 31 located between the section 20 of the elastic hollow element 14 and the end lip 19 thereof. In this way during the introduction of the syringe S, and after the holes 12 are freed, any air which may remain trapped within the chamber 31 can freely escape and not impede the operation of the elastic element 14. Moreover, at the end of the use of the valve connector, when by effect of the removal of the needle-less syringe S the undeformed condition of closure of the elastic head within the inlet fitting 4 and the hermetic closure of the lateral walls 12 are restored, any liquid which may have entered the chamber 31 during use is ejected from the aforesaid holes 29, creating a beneficial positive pressure effect in the outlet fitting 6, 7, facilitating the complete evacuation of all the injected medicament. Lastly, any fluid pressure coming from the outlet fitting 6, 7 can be absorbed within the chamber 31, whilst enabling the sealing characteristics at the complementary conical surfaces 26, 27 to be enhanced.

The passage section of the holes 29 is conveniently calibrated, relative to that of the holes 12, to obtain the effects described above.

Naturally, the construction details and the embodiments may vary widely from what is described and illustrated herein, without thereby departing from the scope of the present invention as defined by the appended claims.

The invention claimed is:

1. A valve connector for medical lines of infusion by means of a fluid introducer, comprising:
   a tubular body having a cavity, an inlet end adapted for the engagement of an introducer, and an outlet end;
   a hollow pin arranged axially within the cavity of the tubular body and having a closed terminal oriented towards said inlet end of the tubular body and axially distanced therefrom, said hollow pin being in communication with the outlet end of the tubular body and having at least a lateral hole distanced from said terminal for communication with the cavity of said tubular body;
   an elastic sealing element, comprising:
      an elastic head having a pre-slotting and normally arranged in a closed condition within said inlet end of the tubular body, in which said pre-slotting is closed, and being axially movable against said terminal of the hollow pin by effect of the insertion of said introducer into the inlet end, to interact with said terminal assuming an elastically deformed open configuration in which the pre-slotting is opened,
      an elastic hollow element joined to said head and interposed between said tubular body and said hollow pin to isolate the cavity of said tubular body relative to said outlet end, said elastic hollow element defining an elastic thrust means tending to maintain said head in said closed condition and having an inner surface to contact said hollow pin to isolate said at least one lateral hole relative to the cavity of the tubular body when said head is in the aforesaid undeformed sealing condition;
      the terminal of the hollow pin being shaped to interact with the head of the elastic sealing element to cause said head to deform such that the pre-slotting is opened without being crossed by said terminal;
      said tubular body positively pressing said inner contact surface of the hollow element of the elastic sealing element against said hollow pin when said elastic head is in the aforesaid closed position; and
      wherein when said elastic head moves from the closed condition to the open configuration, said inner contact surface of the hollow element of the elastic sealing element opens communication between said at least one lateral hole of the hollow pin and the inlet end of the tubular body through said pre-slotting;
   wherein said hollow pin has at least an additional lateral hole axially distanced from said at least one lateral hole at the side of said outlet end of the tubular body.

2. The valve connector as claimed in claim 1, wherein said tubular body has an inner wall portion with conical surface against which contacts, in the aforesaid closed position of said elastic head, a complementary conical surface portion of the hollow element of the elastic sealing element.

3. The valve connector as claimed in claim 2, wherein said complementary conical surface portion of the hollow element of the elastic sealing element is pressed against said hollow pin, when said elastic head is in the aforesaid closed condition, also by the action of an axial pre-load of said hollow element.

4. The valve connector as claimed in claim 3, wherein said hollow element of the elastic sealing element has, in proximity to said elastic head, an outer arresting portion which, in said undeformed condition of sealing of said elastic head, faces a complementary inner arresting surface of the tubular body adjacent to said inlet end.

5. The valve connector as claimed in claim 4, wherein said outer arresting portion and said complementary inner arresting surface have conical shapes.

6. The valve connector as claimed in claim 1, wherein said terminal of the hollow pin has a plurality of axial projections angularly distanced and delimiting between them flow channels facing said head of the elastic sealing element.

7. The valve connector as claimed in claim 6, wherein said projections have ends for interacting with the head of the elastic sealing element having generally flat configuration.

8. The valve connector as claimed in claim 6, wherein said projections have ends for interacting with the head of the elastic sealing element having generally rounded configuration.

9. The valve connector as claimed in claim 6, wherein said elastic head is internally formed with axial flow channels.

10. The valve connector as claimed in claim 1, wherein said hollow element of the elastic sealing element comprises a generally cylindrical non corrugated body.

11. The valve connector as claimed in claim 10, wherein said generally cylindrical non corrugated body has a circular section.

12. The valve connector as claimed in claim 10, wherein said generally cylindrical non corrugated body has an elliptical section.

13. The valve connector as claimed in claim 10, wherein said generally cylindrical non corrugated body has a polygonal section.

14. The valve connector as claimed in claim 1, wherein said inner contact surface of the hollow element of the elastic sealing element is so shaped as to be applied radially against said at least one lateral hole of the hollow pin in its closed condition.

15. The valve connector as claimed in claim 14, wherein said hollow pin is formed, at said at least one lateral hole, with an outer annular throat.

16. The valve connector as claimed in claim 14, wherein said hollow element of the elastic sealing element has an annular bulge defining said inner contact surface.

17. The valve connector as claimed in claim 1, wherein said inner contact surface of the hollow element of the elastic sealing element is so shaped as to be applied radially at a region of said hollow pin situated between said at least one lateral hole and said terminal.

18. The valve connector as claimed in claim 17, wherein said hollow pin has an outer annular shoulder with conical surface and said inner contact surface of the hollow element of the elastic sealing element comprises an inner annular projection having a conical surface complementary to that of said outer annular shoulder.

19. The valve connector as claimed in claim 1, wherein said inlet end of the tubular body has a cylindrical inner surface.

20. The valve connector as claimed in claim 1, wherein said outlet end of the tubular body comprises a male Luer-Lock connection element, and said male Luer-Lock connection element is formed at least in part integrally with said hollow pin.

21. A valve connector for medical lines of infusion by means of a fluid introducer, comprising:
  a tubular body having a cavity, an inlet end adapted for the engagement of an introducer, and an outlet end;
  a hollow pin arranged axially within the cavity of the tubular body and having a closed terminal oriented towards said inlet end of the tubular body and axially distanced therefrom, said hollow pin being in communication with the outlet end of the tubular body and having at least a lateral hole distanced from said terminal for communication with the cavity of said tubular body;
  an elastic sealing element, comprising:
    an elastic head having a pre-slotting and normally arranged in a closed condition within said inlet end of the tubular body, in which said pre-slotting is closed, and being axially movable against said terminal of the hollow pin by effect of the insertion of said introducer into the inlet end, to interact with said terminal assuming an elastically deformed open configuration in which the pre-slotting is opened,
    an elastic hollow element joined to said head and interposed between said tubular body and said hollow pin to isolate the cavity of said tubular body relative to said outlet end, said elastic hollow element defining an elastic thrust means tending to maintain said head in said closed condition and having an inner surface to contact said hollow pin to isolate said at least one lateral hole relative to the cavity of the tubular body when said head is in the aforesaid undeformed sealing condition;
  the terminal of the hollow pin being shaped to cause the head of the elastic sealing element to assume said open configuration without crossing the pre-slotting;
  said tubular body positively pressing said inner contact surface of the hollow element of the elastic sealing element against said hollow pin when said elastic head is in the aforesaid closed position; and
  wherein when said elastic head moves from the closed condition to the open configuration, said inner contact surface of the hollow element of the elastic sealing element opens communication between said at least one lateral hole of the hollow pin and the inlet end of the tubular body through said pre-slotting;
  said inner contact surface of the hollow element of the elastic sealing element shaped so as to be applied radially at a region of said hollow pin situated between said at least one lateral hole and said terminal; and
  said hollow pin having an outer annular shoulder with conical surface and said inner contact surface of the hollow element of the elastic sealing element comprising an inner annular projection having a conical surface complementary to that of said outer annular shoulder.

22. A valve connector for medical lines of infusion by means of a fluid introducer, comprising:
  a tubular body having a cavity, an inlet end adapted for the engagement of an introducer, and an outlet end;
  a hollow pin arranged axially within the cavity of the tubular body and having a closed terminal oriented towards said inlet end of the tubular body and axially distanced therefrom, said hollow pin being in communication with the outlet end of the tubular body and having at least a lateral hole distanced from said terminal for communication with the cavity of said tubular body;
  an elastic sealing element, comprising:
    an elastic head having a pre-slotting and normally arranged in a closed condition within said inlet end of the tubular body, in which said pre-slotting is closed, and being axially movable against said terminal of the hollow pin by effect of the insertion of said introducer into the inlet end, to interact with said terminal assuming an elastically deformed open configuration in which the pre-slotting is opened,
    an elastic hollow element joined to said head and interposed between said tubular body and said hollow pin to isolate the cavity of said tubular body relative to said outlet end, said elastic hollow element defining an elastic thrust means tending to maintain said head in said closed condition and having an inner surface to contact said hollow pin to isolate said at least one lateral hole relative to the cavity of the tubular body when said head is in the aforesaid undeformed sealed condition;
  the terminal of the hollow pin being shaped to interact with the head of the elastic sealing element to cause said head to deform such that the pre-slotting is opened without being crossed by said terminal;

said tubular body positively pressing said inner contact surface of the hollow element of the elastic sealing member against said hollow pin when said elastic head is in the aforesaid closed position; and wherein when said elastic head moves from the closed condition to the open configuration, said inner contact surface of the hollow element of the elastic sealing element opens communication between said at least one lateral hold of the hollow pin and the inlet end of the tubular body through said pre-slotting;

wherein said inner contact surface of the hollow element of the elastic sealing member is so shaped as to be applied radially at a region of said hollow pin situated between said at least one lateral hole and said terminal; and wherein said hollow pin has an outer annular shoulder with conical surface and said inner contact surface of the hollow element of the elastic sealing element comprises an inner annular projection having a conical surface complementary to that of said outer annular shoulder.

* * * * *